(12) United States Patent
Kamiya et al.

(10) Patent No.: US 8,460,526 B2
(45) Date of Patent: Jun. 11, 2013

(54) GAS SENSOR AND PROCESS FOR PRODUCING THE SAME

(75) Inventors: Sumio Kamiya, Toyota (JP); Takashi Ito, Toyohashi (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 212 days.

(21) Appl. No.: 12/894,244

(22) Filed: Sep. 30, 2010

(65) Prior Publication Data

US 2011/0017596 A1    Jan. 27, 2011

Related U.S. Application Data

(63) Continuation of application No. PCT/JP2009/055847, filed on Mar. 24, 2009.

(30) Foreign Application Priority Data

Apr. 7, 2008    (JP) .................................. 2008-099378

(51) Int. Cl.
  *G01N 27/407*    (2006.01)
  *G01N 27/417*    (2006.01)

(52) U.S. Cl.
  USPC ..... 204/424; 204/410; 205/783.5; 205/784.5; 73/23.32

(58) Field of Classification Search
  USPC .................. 204/410, 411, 421–429; 205/781, 205/783.5–785, 787; 73/23.31, 23.32
  See application file for complete search history.

(56) References Cited

U.S. PATENT DOCUMENTS

| | | | |
|---|---|---|---|
| 5,849,165 A | | 12/1998 | Kojima et al. |
| 5,874,664 A | * | 2/1999 | Watanabe et al. ............. 73/23.32 |
| 5,993,725 A | * | 11/1999 | Zuk et al. ...................... 264/635 |
| 2002/0000116 A1 | | 1/2002 | Kimata et al. |
| 2003/0116435 A1 | * | 6/2003 | Satou et al. .................... 204/424 |

FOREIGN PATENT DOCUMENTS

| CN | 1251330 A | 4/2000 |
|---|---|---|
| CN | 1796991 A | 7/2006 |

(Continued)

OTHER PUBLICATIONS

International Search Report in International Application No. PCT/JP2009/055847; Mailing Date: Jun. 30, 2009.

(Continued)

*Primary Examiner* — J. Christopher Ball
(74) *Attorney, Agent, or Firm* — Finnegan, Henderson, Farabow, Garrett & Dunner, LLP (57) ABSTRACT

A sealing portion is formed of a calcined body that is made by calcining a powder compact of a spherically-shaped granulated powder that is selected from the group consisting of alumina, aluminum titanate and cordierite. Anisotropy in physical properties is less likely to occur in the powder compact, because these ceramics are not only good in terms of thermal stability but also their spherically-shaped granulated powders are less likely to be oriented at the time of powder compacting. Therefore, the sealing portion comes to have a long longevity, because slippages between the particles are less likely to occur even when thermal histories are applied thereto, and because it can maintain the gas sealing property stably for a long period of time.

4 Claims, 4 Drawing Sheets

FOREIGN PATENT DOCUMENTS

| | | |
|---|---|---|
| EP | 1 167 958 | 1/2002 |
| JP | 63-16356 | 4/1988 |
| JP | 7-333191 | 12/1995 |
| JP | 10-132779 | 5/1998 |
| JP | 2000-121599 | 4/2000 |
| JP | 2002-82088 | 3/2002 |
| JP | 2005-306625 | 11/2005 |

OTHER PUBLICATIONS

Zhipeng, X. et al., "Study on Binder Removal Process of Ceramic Injection Molding," Bulletin of the Chinese Ceramic Society, vol. 2, 1998, pp. 1-7.

Extended European Search Report for EP Appl. No. 09729591.9 dated Mar. 17, 2011.

* cited by examiner

GAS SENSOR AND PROCESS FOR PRODUCING THE SAME

This is a continuation of PCT application PCT/JP2009/055847 filed Mar. 24, 2009, which in turn is based on Japanese application No. 2008-99,378 filed Apr. 7, 2008, the entire contents of each of which is incorporated herein by reference.

TECHNICAL FIELD

The present invention relates to a gas sensor that detects an oxygen concentration and the like in exhaust gases, and to a process for manufacturing the same.

BACKGROUND ART

An oxygen sensor for detecting an oxygen concentration in exhaust gases has been installed to the exhaust system of automobile, and its signals have been used for the feedback control of air-fuel ratio, and the like. Moreover, they have also been used for the judgment on the degradation degree of catalyst for converting exhaust gases, and so forth.

As for this oxygen sensor, those which employ a solid electrolyte such as zirconia have been used widely in recent years. In general, these solid electrolyte-type oxygen sensors are one that has a test-tube configuration, and which is equipped with: a cylinder-shaped detector element comprising a solid electrolyte and having opposite ends one of which is closed; a reference electrode being put in place on the inner side of the detector element; and a measurer electrode being formed on an outer circumferential surface of the bottom in the detector electrode. The detector electrode is accommodated in a hollow case, and is then fixed to it; the air serving as an interference gas is introduced into the interior of the detector element; and the closed leading end of the detector electrode faces an empty space into which a gas to be measured is introduced.

In such a gas sensor, the gas sealing property between the detector element and the case is important in order to restrict the mixing of the gas to be measured with the interference gas such as the air. To put it differently, it is important to maintain the ventilation volume stably at a predetermined value for a long period of time. Hence, in Japanese Unexamined Patent Publication (KOKAI) Gazette No. 2000-121,599, a structure is set forth, structure in which a sealing powder comprising talc is filled in a gap between the outer circumferential surface of a detector element and the inner circumferential surface of a case, and in which this gap is sealed air-tightly by raising its filling density.

Patent Literature No. 1: Japanese Unexamined Patent Publication (KOKAI) Gazette No. 2000-121,599

DISCLOSURE OF THE INVENTION

Assignment to be Solved by the Invention

However, in a gas sealing structure in which a powder for sealing is used, there is a limitation on the durability in the gas sealing property even when the filling density is raised, and so a further improvement of the long-term stability in the gas sealing property has been desired. Moreover, it has also become apparent that anisotropy occurs in characteristics due to orientations at the time of filling, depending on materials for the sealing powder.

After a powder for sealing has been filled in a gap between the outer circumferential surface of a detector element and the inner circumferential surface of a case, it is compressed upward and downward so that it swells out in diametric directions; and then it is brought into press contact with the outer circumferential surface of the detector element and the inner circumferential surface of the case, thereby having it exhibit a sealing power. However, since talk that is used as a sealing powder is scale-like particles, its wider surfaces orient lamellarly in parallel to the vertical direction with respect to the compression direction. Therefore, in the resulting powder compact that seals the gap, the thermal expansion coefficient in the up/down direction (or compression direction), and that in the diametric directions have come to differ from each other.

When anisotropy thus occurs in the thermal expansion coefficient, there might arise such a case that the gas sealing property declines because slippages are caused between the particles by means of thermal histories at the time of service. Especially, in recent automotive applications, the replacement timing of gas sensors has come earlier because the temperature of exhaust gases rises remarkably due to the improvements in engine performance, the change of combustion into lean burning, and the like.

The present invention is one which has been done in view of the aforementioned circumstances, and it is an assignment to adapt gas sensor into longer lasting one which can maintain the gas sealing property in a gap between the outer circumferential surface of detector element and the inner circumferential surface of case stably for a long period of time, that is, which can maintain the ventilation volume at a predetermined value stably for a long period of time.

Means for Solving the Assignment

A characteristic of a gas sensor according to the present invention which solves the aforementioned assignment lies in that:

it is a gas sensor being equipped with:

a cylinder-shaped case;

a cylinder-shaped detector element being inserted into the inside of the case and then being put in place therein, comprising a solid electrolyte, and having opposite ends one of which is closed;

a ring-shaped sealing portion filling a gap between an outer circumferential surface of the detector element and an inner circumferential surface of the case to seal the gap while maintaining a predetermined ventilation volume, thereby restricting the mixing of an interference gas with a gas to be measured; and the sealing portion comprising a calcined body that is made by calcining a powder compact of a spherically-shaped granulated powder that is selected from the group consisting of alumina, aluminum titanate and cordierite.

Moreover, a characteristic of a manufacturing process for gas sensor according to the present invention lies in that:

it is a process for manufacturing a gas sensor being equipped with:

a cylinder-shaped case;

a cylinder-shaped detector element being inserted into the inside of the case and then being put in place therein, comprising a solid electrolyte, and having opposite ends one of which is closed;

a ring-shaped sealing portion filling a gap between an outer circumferential surface of the detector element and an inner circumferential surface of the case to seal the gap while maintaining a predetermined ventilation volume, thereby restricting the mixing of an interference gas with a gas to be measured; and the following are carried out:

a powder compacting step of subjecting a mixture powder to powder compacting, the mixture powder being made by adding an organic binder to a spherically-shaped granulated powder that is selected from the group consisting of alumina, aluminum titanate and cordierite, to powder compacting, thereby forming a ring-shaped powder compact that includes the organic binder;

a crimping step of loading the powder compact in a gap between an outer circumferential surface of the detector element and an inner peripheral surface of the case, and then crimping the case from an outer circumferential surface thereof, thereby fixing the powder compact in the gap;

a degreasing step of removing the organic binder from the powder compact that has been fixed in the gap; and a calcining step of calcining the powder compact that has undergone the degreasing step.

Effect of the Invention

In accordance with a gas sensor according to the present invention, a calcined body, which is made by calcining a powder compact of a spherically-shaped granulated powder that is selected from the group consisting of alumina, aluminum titanate and cordierite, is used for the sealing portion. Since these ceramics are good in terms of thermal stability and additionally their spherically-shaped granulated powders are less likely to orient at the time of powder compacting, anisotropy in physical properties is less likely to occur in the resulting powder compacts. Therefore, it is possible to secure sensor accuracy that is stable for a long period of time because the slippages between particles are less likely to occur even when thermal histories are applied thereto, and because change with time is less likely to occur in the gas sealing property.

Moreover, in accordance with the manufacturing process for gas sensor according to the present invention, since a powder compact is loaded in a gap between the outer circumferential surface of a detector element and the inner circumferential surface of a case, the loading is easy. And, since the powder compact deforms as being accompanied by the deformation of the case in the crimping step, such a drawback that the detector element cracks is prevented, and then the powder compact is brought into press contact with the outer circumferential surface of the detector element and the inner circumferential surface of the case in the same manner as conventional powder filling. By carrying out degreasing and calcining in that state, the powder compact is calcined in such a state that it has made press contact with the outer circumferential surface of the detector element and the inner circumferential surface of the case.

By means of this setting, the gas sensor according to the present invention is manufactured. Note that no such a problem arises that the gas sealing property has been enhanced excessively, because sintering occurs between particles within the powder compact at the time of sintering so that it becomes feasible to adjust the pore distribution or the pore diameters by setting up the calcination conditions suitably.

EXPLANATION ON REFERENCE NUMERALS

1: Detector Element;
2: Heater;
3: Casing;
4: Protector;
5: Sealing Portion;
6: Spacer;
7: Outer Cylinder; and
50: Powder Compact

BEST MODE FOR CARRYING OUT THE INVENTION

A gas sensor according to the present invention is equipped with a case, a detector element, and a sealing portion. The case is one which makes a cylindrical shape, and is made of metal.

The detector element is one which is the same as conventional ones that comprise a solid electrolyte, have opposite ends one of which is closed, and makes a cylinder-shaped test-tube configuration. As for the solid electrolyte, it is possible to use one which is the same as conventional ones, such as stabilized zirconia which enables oxygen ions to come in and go out. A reference electrode is formed inside the detector element, and a measurer electrode is formed outside the detector element.

The reference electrode is formed on an inner circumferential surface of the detector element; in general, it is formed on the entire face at a part that faces the measurer electrode. This reference electrode can be formed of platinum, or the like, which has a function of oxygen dissociating catalyst, in the same manner as heretofore.

The measurer electrode is generally formed on an outer circumferential surface at the bottom of the detector element. By forming it thusly on the bottom, it is likely to be exposed to exhaust gases, and it makes it possible to shorten the response time. This measurer electrode can also be formed of platinum, or the like, which has a function of oxygen dissociating catalyst, in the same manner as heretofore. Moreover, on each of the opposite-end sides of the detector element, a terminal connector is formed, terminal connector which possesses a function of transmitting electromotive forces being generated at the detector element to the outside by way of a signal line and so forth, and which is connected to the reference electrode or the measurer electrode.

It is desirable to form an electrode protector layer, a trap layer, and the like, on some of the surfaces of the detector element on which neither the measurer electrode, the terminal connectors, nor these are formed. In the same manner as heretofore, the electrode protector layer can be formed of alumina, mullite, $MgO$—$Al_2O_3$ spinel, or the like; and the trap layer can be formed of alumina, or the like.

The sealing portion that makes one of the characteristics of the present invention fills a gap between an outer circumferential surface of the detector element and an inner circumferential surface of the case to seal the gap, and thereby the ventilation volume of gas is maintained at a predetermined value so that a mixed amount of an interference gas with a gas to be measured is kept being constant. This sealing portion comprises a calcined body that is made by calcining a powder compact of a spherically-shaped granulated powder that is selected from the group consisting of alumina, aluminum titanate and cordierite. It is also allowable to form the sealing portion of a single-product spherically-shaped granulated powder of one of these raw materials, or it is even possible to form the sealing portion of multiple species of spherically-shaped granulated powders that are selected from these raw materials.

Since each ceramic powder that is selected from the group consisting of alumina, aluminum titanate and cordierite has a configuration that is spherical, orientation is less likely to occur at the time of powder compacting. Therefore, the slippages between the particles are less likely to occur even when thermal histories are applied thereto, because anisotropy is less likely to occur in the thermal expansion coefficient of the calcined body; and it is possible to secure sensor accuracy that is stable for a long period of time, because change with time is less likely to occur in the gas sealing property.

Moreover, each powder compact that comprises a spherically-shaped granulated powder being selected from the group consisting of alumina, aluminum titanate and cordierite is good in terms of thermal stability after the organic binder has been removed, and so degenerations hardly occur at the time of service as a gas sensor. Therefore, it is possible to maintain the initial gas sealing property stably for a long period of time.

In order to maintain properties as the sealing portion for a long period of time, it is preferable that a porosity of the calcined body can be 25-55%; and it is furthermore desirable that it can be 30-50%. Moreover, it is preferable that an average pore diameter of the calcined body can be 0.06-0.6 µm; and it is furthermore desirable that it can be 0.07-0.59 µm. When the porosity or average pore diameter becomes greater than this range, the gas sealing property becomes insufficient; whereas the gas ventilation volume declines when making the porosity or average pore diameter smaller than this range.

In order to set the porosity and average pore diameter in the aforementioned ranges, it is necessary to put the following under control appropriately: types of spherically-shaped granulated powders to be used; particle diameters thereof; binders to be used for granulating the spherically-shaped granulated powders; calcining temperatures; and the like. When using a spherically-shaped granulated powder being made of alumina, it is desirable to use $\alpha$-$Al_2O_3$ that is good in terms of heat resistance; and those whose average particle diameter is 30-90 µm is preferable. Moreover, it is possible to set the calcining temperature to 600-1,250° C.

When using a spherically-shaped granulated powder being made of aluminum titanate (i.e., $Al_2TiO_5$), its average particle diameter can preferably be 30-90 µm; and it is preferable to set the calcining temperature to 600-1,250° C. Moreover, when using a spherically-shaped granulated powder being made of cordierite, it is preferable to use one that has the $2MgO$-$2Al_2O_3$-$5SiO_2$ composition; its average particle diameter can preferably be 30-90 µm; and it is preferable to set the calcining temperature to 600-1,250° C.

When manufacturing a gas sensor that possesses the sealing portion according to the present invention, a ring-shaped powder compact is formed of a spherically-shaped granulated powder, which is selected from the group consisting of alumina, alumina titanate and cordierite, by means of powder compacting in the first place. Since an organic binder is included in the spherically-shaped granulated powder, a configuration of the resulting powder compact is maintained.

Note that spherically-shaped granulated powders are formed by methods being called "spray drying" in general. That is, each of the ceramic powders is dispersed in water, and an organic binder is added at that time. The resulting slurry is sprayed to turn it into spherically-shaped particles, and then the water content is removed while they undergo free falling, and thereby it is possible to obtain each of the spherically-shaped granulated powders in which the powders are combined with each other by means of the organic binder.

Therefore, in order to maintain a configuration of the powder compact, such an amount of the organic binder that is included in each of the spherically-shaped granulated powders would be satisfactory; however, it is allowable as well to mix another organic powder therewith in an adequate amount before powder compacting, if it should run short.

The organic binder being included each of the spherically-shaped granulated powders, or the other organic binder to be added is one which maintains a configuration of the powder compact, and it is possible to use the following therefor: polyvinyl alcohol, methyl cellulose, acrylic resins, and the like. Although their amount depends on types of the ceramic powders slightly, it is desirable to set it to 0.1-10 parts by mass with respect to 100 parts by mass of the ceramic powders. When the amount of the organic binders is greater than this range, the porosity of the resultant sintered bodies becomes too high to be sufficient in the gas sealing property; whereas maintaining a configuration of the powder compact becomes difficult when the amount of the organic binders is less than this range.

It is desirable that an inorganic binder can be further included in the powder compact. The strength of the resulting calcined body is upgraded by including an inorganic binder so that it is possible to maintain the configuration, and thereby it is possible to prevent configurational change with time from resulting in changing the gas sealing property. As for such an inorganic binder, it is possible to use the following: alumina sol, colloidal silica, sodium silicate, phosphate-based binders, metallic alkoxide-based binders, and the like.

It is desirable to set an addition amount of the inorganic binder to 1.0-10.0 parts by mass with respect to 100 parts by mass of the ceramic powder. When the addition amount of the inorganic binder is greater than this range, it becomes difficult to get control over the porosity of the resultant sintered body; whereas there might be cases where the strength of the sintered body is degraded by means of the migration of particles in service when it is less that this range.

When forming the powder compact, it is preferable to set a pressure at the time of powder compacting to 2 MPa or more. When the compacting pressure is lower than this, not only it becomes difficult to maintain a configuration of the powder compact, but also it becomes difficult to put the porosity of the resultant calcined body under control.

It is desirable to set the calcining temperature to 600-1, 250° C. as aforementioned. When the calcining temperature is lower than this range too much, the gas sealing property becomes likely to change; whereas the porosity has declined when it is too high so that it becomes difficult to control the resulting gas sensor.

Note that, although the degreasing step can be generally carried out at a temperature of 350-500° C., a temperature that is lower than that of the calcining step, it is also feasible that a temperature increasing step during the calcining step can double as the degreasing step.

EXAMPLES

Hereinafter, the present invention will be explained in detail by means of examples and testing examples.

Example No. 1

Figure 1:
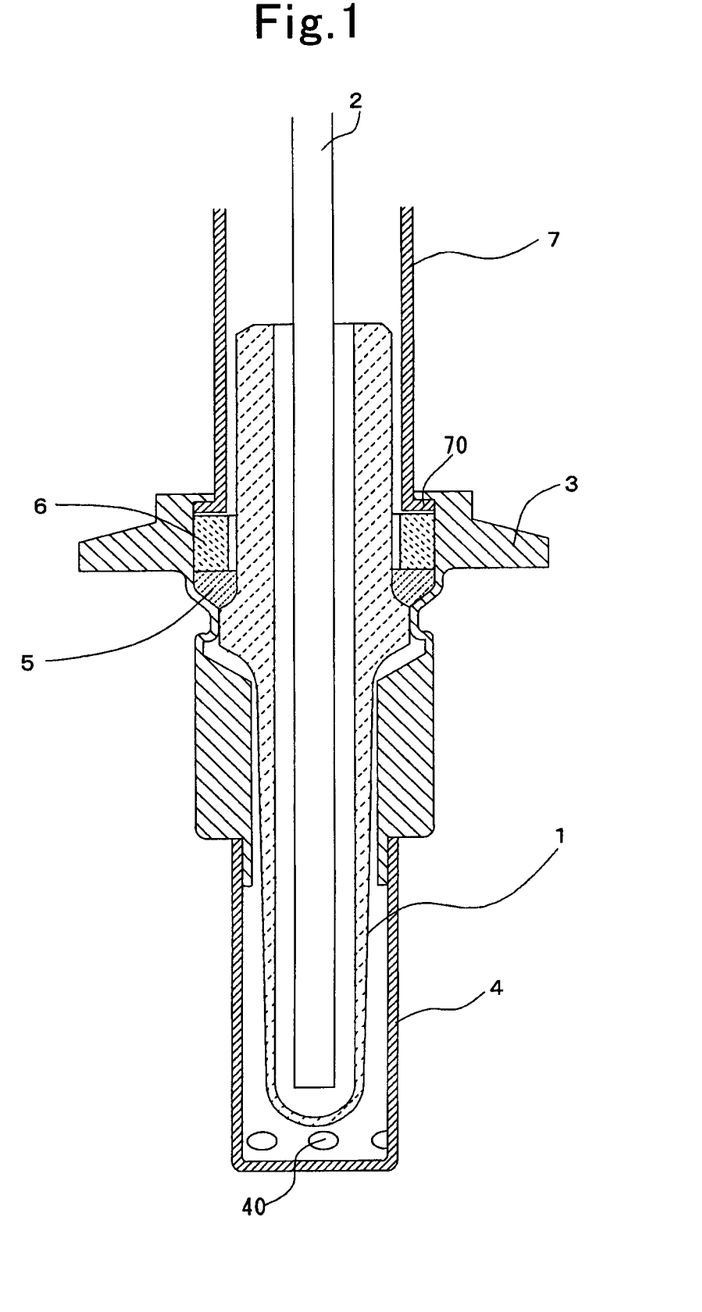
FIG. 1 is a cross-sectional diagram of a major part of an oxygen sensor that is directed to one of examples according to the present invention.

In FIG. 1, a cross-sectional diagram of a major part of an oxygen sensor that is directed to the present example is illustrated. This oxygen sensor is constituted of the following: a detector element 1 that is formed as a bottomed cylindrical shape and makes a test tube configuration; a heater 2 that is disposed inside the detector element 1, and which is formed as a rod shape and is made of ceramic; a casing 3 that accommodates the detector element 1 and heater 2 therein; a cylindrical protector 4 that is installed to the lower opposite end of the casing 3 and covers the bottom of the detector element 1 which projects from the lower opposite end of the casing 3; and a ring-shaped sealing portion 5 that is put in place in a gap between the outer circumferential surface of the detector element 1 and the inner circumferential surface of the casing 3; and additionally a spacer 6 that is made of cylinder-shaped ceramic; and an outer cylinder 7 that is fixed to the upper opposite end of the casing 3.

The sealing portion 5 fills the gap between the outer circumferential surface of the detector element 1 and the inner circumferential surface of the casing 3 to seal therebetween. Moreover, it makes it feasible to introduce the air into the interior of the detector element 1 by way of the outer cylinder 7. The protector 4, which is made of metal, is provided with a plurality of through holes 40 that penetrates between the inside and the outside, and is thereby constituted so as to expose the bottom of the detector element 1 to exhaust gases.

Figure 2:
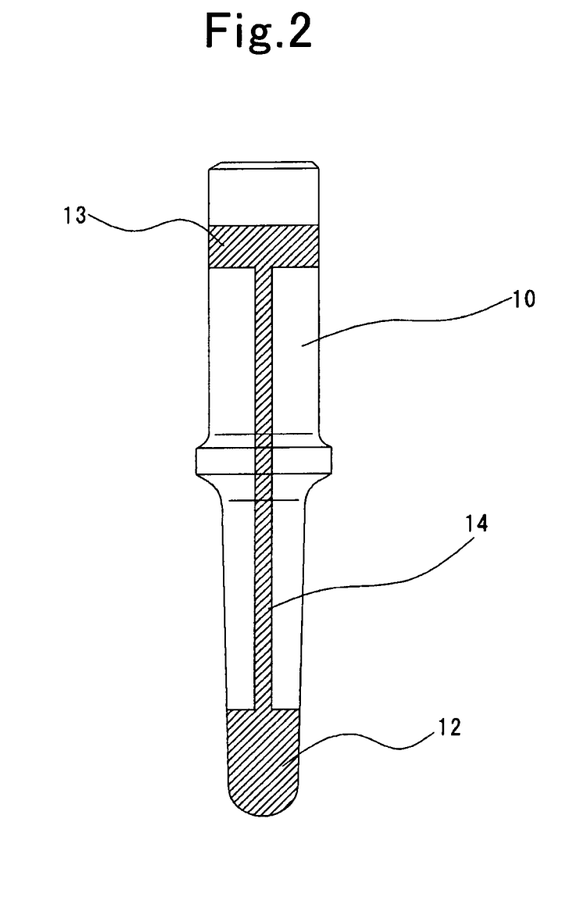
FIG. 2 is a front-view diagram for illustrating a detector element, which is used in the gas sensor that is directed to the one of examples according to the present invention, in such a state that an electrode protector layer and a trap layer are removed.
Figure 3:
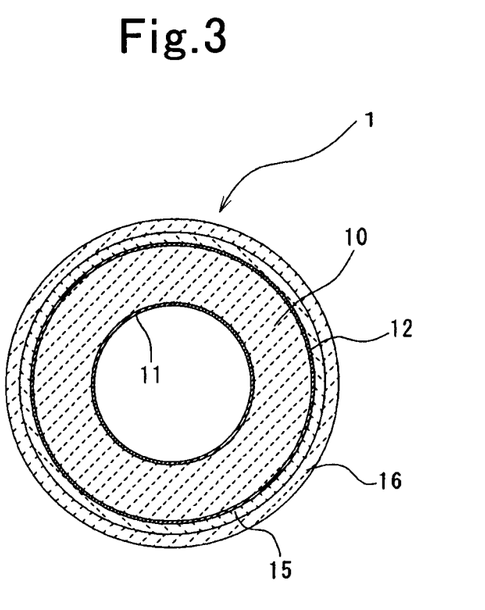
FIG. 3 is a cross-sectional diagram of the detector element, which is used in the gas sensor that is directed to the one of examples according to the present invention.

As illustrated in FIG. 2 and FIG. 3, the detector element 1 is equipped with a test-tube-configured elemental portion 10 in which stabilized zirconia makes the major component. A reference electrode 11, which comprises platinum, is formed on the inner circumferential surface of the elemental portion 10 over the entire surface. Moreover, a measurer electrode 12, which comprises platinum, is formed on the outer surface of the bottom in the elemental portion 10, and a terminal connector portion 13, which comprises platinum, is formed on the outer circumferential surface of the other end that is on the opposite side to the bottom. The measurer electrode 12 is formed as a cup shape that covers the entire surface of the bottom, and the terminal connector portion 13 is formed as a ring shape that goes around the elemental portion 10. And, a leader portion 14, which connects the measurer electrode 12 with the terminal connector 13 electrically, is formed on the outer circumferential surface of the elemental portion 10. The measurer electrode 12, terminal electrode 13 and leader portion 14 are formed by printing a platinum paste.

And, the following are formed on a surface of the elemental portion 10: an electrode protector layer 15 that covers the measurer electrode 12 and leader portion 14, and which covers an exposed surface of the elemental portion 10 on which no measurer electrode 12 and leader portion 14 are formed; and a trap layer 16 that covers the electrode protector layer 15. The electrode protector layer 15 is formed of $MgO$—$Al_2O_3$ spinel, and the trap layer 16 is formed of $\gamma$-$Al_2O_3$ spinel.

The reference electrode 11 and terminal connector portion 13 are connected to a not-shown voltmeter by way of not-illustrated extraction lines. And, the protector 4 is put in place so as to be exposed to exhaust gases, and then an electric power source for the heater 4 is turned on electrically to heat the heater 4. By means of this setting, the elemental portion 10 is heated so that it is activated; accordingly, the coming in and going out of oxygen ions become active therein; consequently an electromotive force, which is in compliance with the difference between oxygen concentrations, generates between the measurer electrode 12, which is exposed to an atmosphere of the exhaust gases, and the reference electrode 11, which is exposed to an atmosphere of the air. An oxygen concentration in the exhaust gases is detected by measuring the resulting electromotive force.

Incidentally, the sealing portion 5 is formed of $\alpha$-alumina granules in the oxygen sensor according to the present example. Hereinafter, a process for manufacturing this oxygen sensor will be explained instead of explanations on the construction of the sealing portion 5.

First of all, $\alpha$-alumina granules (i.e., aspherically-shaped granulated powder), which contained polyvinyl alcohol that served as an organic binder in an amount of 0.5% by mass as the solid content, were made ready, and were then powder compacted by a pressure of 2 MPa by means of pressing using a die, thereby forming a ring-shaped powder compact. The resulting powder compact was impregnated with a predetermined amount of an inorganic-binder aqueous solution in which sodium silicate was dissolved in a prescribed concentration, and was then dried, thereby making a powder compact 50 that included sodium silicate in an amount of 3% by mass as the solid content.

Figure 4:
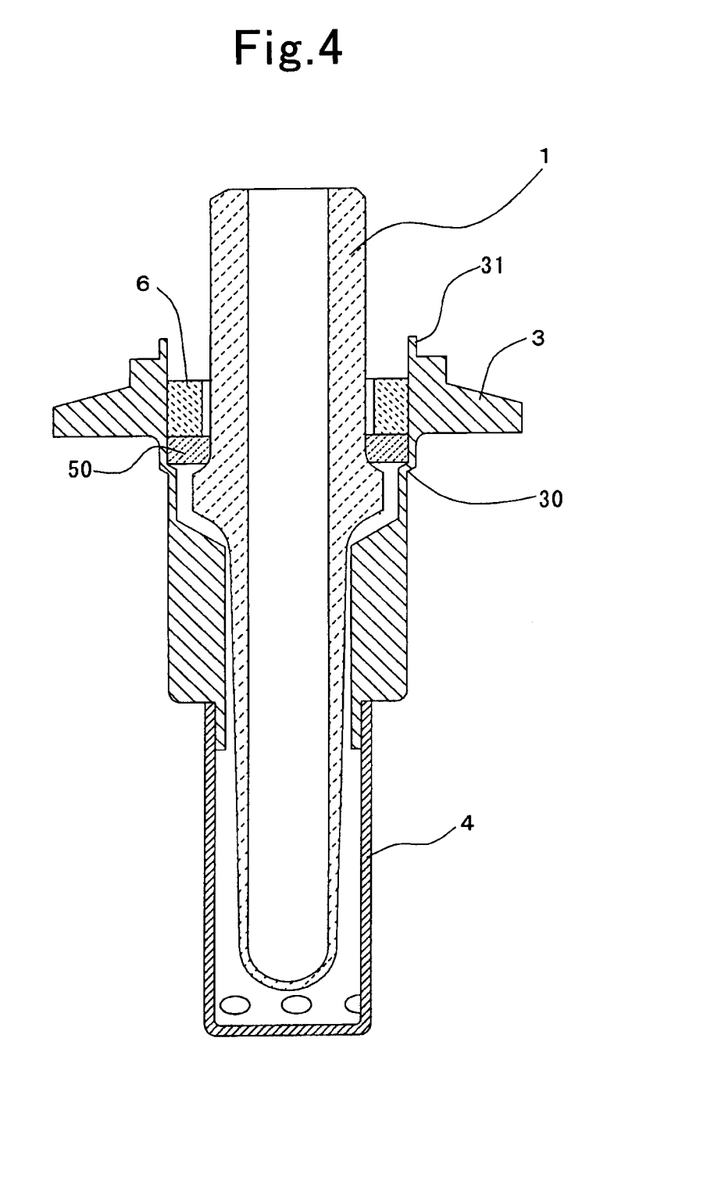
FIG. 4 illustrates a manufacturing process for gas sensor that is directed to the one of examples according to the present invention, and is a cross-sectional diagram of a state before crimping a casing to fix a powder compact therein.

Meanwhile, a subassembly was made ready, subassembly which was made as follows: the casing 3, and the protector 4 were fixed to each other by means of crimping, and the detector element 1 was then inserted into their interior. Moreover, the powder compact 50 was put in place in a gap between the casing 3 and the detector element 1, as illustrated in FIG. 4; in addition, a spacer 6 being made of alumina was put in place on the powder compact 50. While pressurizing the powder compact 50 by way of the spacer 6, the casing 3 was crimped by reducing it diametrically from the outer circumference at its thin-walled section 30 that corresponds to the lower section of the powder compact 50, and thereby the powder compact 50 was fixed. In this instance, the casing 3 underwent plastic deformation, and the powder compact 50 was thereby brought into press contact with the detector element 1, casing 3 and spacer 6.

The resultant assembly was heated to 450° C. and was then held thereat for 1 hour in that state, there by degreasing the polyvinyl alcohol that was included in the powder compact 50. Moreover, the assembly was further heated to 600° C. and was then held thereat for 1 hour, thereby calcining the powder compact 50. By doing thusly, the sealing portion 5 was formed, sealing portion 5 which was brought into press contact with the detector element 1, casing 3 and spacer 6, and which fills a gap between the outer circumferential surface of the detector element 1 and the inner circumferential surface of the casing 3.

Thereafter, an outer cylinder 7 that possessed a flanged section 70 is put in place in the upper part of the casing 3, and then a thin-walled cylindrical section 31, which protrudes from the top end of the casing 3, was crimped, and thereby the casing 3 and the outer cylinder 7 were fixed to each other. On this occasion, the spacer 6 was furthermore brought into press contact with the sealing portion 5. And, the heater 2 was inserted into the interior of the detector element 1, thereby obtaining the gas sensor according to the present example.

Testing Example No. 1

Using the $\alpha$-alumina granules that were used in Example No. 1, cylindrical-column-configured pellets with 18 mm in diameter and 10 mm in height were made by powder compacting them by a pressure of 2 MPa by means of pressing using a die. The resulting pellets were heated for 1 hour, respectively, at each of the following temperatures: 600° C., 750° C., 800° C., 1,050° C., 1,150° C., and 1,250° C. Then, each of the resultant calcined bodies was measured for the pore volume, median pore diameter and porosity, respectively. The results are shown in Table 1.

For comparison, a powder compact, which was made by powder compacting in the same manner as aforementioned but using a talc powder that has been used heretofore (containing polyvinyl alcohol that served as an organic binder in an amount of 0.5% by mass as the solid content), was measured for the pore volume, median pore diameter and porosity, respectively. The results are shown in Table 1 in conjunction with the above-mentioned.

TABLE 1

| Calcining Temp. (° C.) | Pore Volume (mL/g) | Pore Diameter (μm) | Porosity (%) |
|---|---|---|---|
| 600 | 0.27 | 0.07 | 52 |
| 750 | 0.28 | 0.08 | 52 |
| 800 | 0.27 | 0.07 | 54 |
| 1050 | 0.29 | 0.09 | 53 |
| 1150 | 0.27 | 0.09 | 50 |
| 1250 | 0.21 | 0.08 | 44 |
| Talc Powder Compact | 0.14 | 0.20 | 40 |

From Table 1, it is understood that the porosity was hardly changed by calcination, which was done at less than 1,250° C., in the alumina calcined bodies, and that the sintering progressed in part because the porosity and pore volume decreased when it was done at 1,250° C. And, since a porosity that was virtually equivalent to that of the conventional talc powder compact was exhibited even after undergoing calcination that was done at 1,250° C., it is understood that a gas sealing property that was equivalent to that of the talc powder compact would be demonstrated.

Testing Example No. 2

Using the α-alumina granules that were used in Example No. 1, rod-shaped test specimens with a quadrangle-shaped-columnar configuration that had 3 mm in width, 4 mm in length and 10 mm in height were made by powder compacting them by a pressure of 30 MPa by means of pressing using a die. The resulting rod-shaped test specimens were heated for 1 hour, respectively, at each of the following temperatures: 600° C., 750° C., 850° C., 950° C., and 1,250° C. Then, each of the resultant calcined bodies was measured for the linear expansion magnitude in a temperature zone at an interval from room temperature and up to 800° C., and then the average thermal expansion coefficient was calculated. The results are shown in Table 2.

For comparison, a powder compact, which was made by powder compacting in the same manner as aforementioned but using a talc powder that has been used heretofore (containing polyvinyl alcohol that served as an organic binder in an amount of 0.5% by mass as the solid content), was measured for the linear expansion magnitude and average thermal expansion coefficient similarly. The results are shown in Table 2. In the talc powder compact, since greater differences were appreciated between the pressurizing direction at the time of powder compacting and the other directions (e.g., the right-angled direction thereto), the measurement was carried out in two directions, the pressurizing direction and a right-angled direction with respect to the pressurizing direction. In the alumina calcined bodies, no difference was appreciated between the pressurizing direction at the time of powder compacting and the other directions (e.g., the right-angled direction thereto).

Note that a thermomechanical analyzer ("TMA8310" produced by RIGAKU Co., Ltd.) was used for the measurements, and that the measurements were done under the following conditions: the atmosphere: in the air; the standard sample: quartz glass; and the employed thermocouple: an R-type thermocouple.

TABLE 2

| | Calcining Temp. (° C.) | Linear Expansion Magnitude (%) | Thermal Expansion Coefficient (×10$^{-6}$/° C.) |
|---|---|---|---|
| Alumina Calcined Body | 650 | 0.56 | 7.3 |
| | 750 | 0.60 | 7.8 |
| | 850 | 0.61 | 7.9 |
| | 950 | 0.61 | 8.0 |
| | 1250 | 0.61 | 8.0 |
| Talc Powder Compact | Pressurizing Direction | 1.48 | 19.0 |
| | Square-angled Direction | 0.51 | 6.6 |

In the alumina calcined bodies, it is apparent from Table 2 that the deformations would be less likely to occur at the time of service as a gas sealer than in the talc powder compact, and that the degradation of the gas sealing properties that results from the migrations of the particles would be inhibited, because of the following: the linear expansion magnitudes were considerably less than that of the talc powder compact when being measured in the pressurizing direction; and the average thermal expansion coefficients were smaller as well. Moreover, regarding the thermal expansions of the alumina calcined bodies, no significant differences resulting from the calcining temperatures were recognized.

Testing Example No. 3

Instead of using the α-alumina spherically-shaped granulated powder, using aluminum titanate granules that contained polyvinyl alcohol serving as an organic binder in an amount of 0.5% by mass as the solid content, cylindrical-column-configured pellets were formed by powder compacting them in the same manner as Testing Example No. 1. The resulting pellets were heated for 1 hour, respectively, at each of the following temperatures: 600° C., 750° C., 950° C., and 1,250° C. Then, each of the resultant calcined bodies was measured for the pore volume, median pore diameter and porosity, respectively. The results are shown in Table 3.

TABLE 3

| Calcining Temp. (° C.) | Pore Volume (mL/g) | Pore Diameter (μm) | Porosity (%) |
|---|---|---|---|
| 600 | 0.22 | 0.34 | 44 |
| 750 | 0.21 | 0.32 | 43 |
| 950 | 0.21 | 0.34 | 45 |
| 1250 | 0.14 | 0.59 | 31 |
| Talc Powder Compact | 0.14 | 0.20 | 40 |

In the aluminum titanate calcined bodies, it is understood from Table 3 that the porosities were hardly changed by the calcination that was done at less than 1,250° C., and that the sintering progressed when it was done at 1,250° C., because the porosity and pore volume decreased greatly. And, even after being calcined at 1,250° C., it is understood that a porosity that was virtually equivalent to that of the conventional talc powder compact was shown, and that a gas sealing property that would be equivalent to that of the talc powder compact would be demonstrated.

Testing Example No. 4

Using the same aluminum titanate granules as those used in Testing Example No. 3, rod-shaped test specimens were made by powder compacting them in the same manner as Testing Example No. 2. The resulting rod-shaped test specimens were heated for 1 hour, respectively, at each of the following temperatures: 600° C., 750° C., 950° C., and 1,250° C. Then, the linear expansion magnitude and average thermal expansion coefficient were calculated for each of the resultant calcined bodies in the same manner as Testing Example No. 2. Note that, in the measurements of the linear expansion magnitude and average thermal expansion coefficient, the measurements were carried out in two directions, the pressurizing direction at the time of powder compacting and a right-angled direction with respect to the pressurizing direction. The results are shown in Table 4.

TABLE 4

| | | Pressurizing Direction | | Right-angled Direction to Pressurizing Direction | |
|---|---|---|---|---|---|
| | Calcining Temp. (° C.) | Linear Expansion Magnitude (%) | Thermal Expansion Coefficient ($\times 10^{-6}$/° C.) | Linear Expansion Magnitude (%) | Thermal Expansion Coefficient ($\times 10^{-6}$/° C.) |
| Aluminum Titanate Sintered Body | 600 | 0.55 | 7.2 | 0.48 | 6.2 |
| | 750 | 0.51 | 6.6 | 0.45 | 5.9 |
| | 950 | 0.45 | 5.8 | 0.41 | 5.4 |
| | 1250 | 0.42 | 5.4 | 0.38 | 5.0 |
| Talc Powder Compact | | 1.48 | 19.0 | 0.51 | 6.6 |

In the linear expansion magnitudes and average thermal expansion coefficients of the aluminum titanate calcined bodies, it is seen from Table 4 that no significant differences, which resulted from the pressurizing direction at the time of powder compacting, were recognized. And, it is apparent that the deformations would be less likely to occur in the aluminum titanate calcined bodies at the time of service as a gas sealer, and that the degradation of the gas sealing properties that results from the migrations of the particles would be inhibited therein, because of the following: the linear expansion magnitudes were less than that of the talc powder compact in either one of the directions, in the pressurizing direction and in the right-angled direction to the pressurizing direction; and the average thermal expansion coefficients were small as well.

Testing Example No. 5

Instead of using the alumina granulates, using cordierite granules (produced by MARUMI TOHRYO) that contained polyvinyl alcohol serving as an organic binder in an amount of 0.5% by mass as the solid content, cylindrical-column-configured pellets were formed by powder compacting them in the same manner as Testing Example No. 1. The resulting pellets were heated for 1 hour, respectively, at each of the following temperatures: 600° C., 750° C., 950° C., and 1,250° C. Then, each of the resultant calcined bodies was measured for the pore volume, median pore diameter and porosity, respectively, in the same manner as Testing Example No. 1. The results are shown in Table 5.

TABLE 5

| Calcining Temp. (° C.) | Pore Volume (mL/g) | Pore Diameter (μm) | Porosity (%) |
|---|---|---|---|
| 600 | 0.37 | 0.34 | 51 |
| 750 | 0.35 | 0.33 | 49 |
| 950 | 0.36 | 0.34 | 49 |
| 1250 | 0.33 | 0.35 | 45 |
| Talc Powder Compact | 0.14 | 0.20 | 40 |

In the cordierite calcined bodies, it is understood from Table 5 that the sintering hardly progressed when the calcining temperature fell in a range of up to 1,250° C. And, even after being calcined at 1,250° C., it is presumed that the pore diameter distribution would be present on a larger diameter side slightly but fell in a permissible range. And, it is understood that a gas sealing property that would be equivalent to that of the talc powder compact would be demonstrated, because it is possible to make the pore diameter distribution denser and finer by making the particle diameter of powder smaller, or by enhancing the pressure at the time of powder compacting.

Testing Example No. 6

Using the same cordierite granules as those used in Testing Example No. 5, rod-shaped test specimens were made by powder compacting them in the same manner as Testing Example No. 2. The resulting rod-shaped test specimens were heated for 1 hour, respectively, at each of the following temperatures: 600° C., 750° C., 950° C., and 1,250° C. Then, the linear expansion magnitude and average thermal expansion coefficient were calculated for each of the resultant calcined bodies in the same manner as Testing Example No. 2. Note that, in the measurements of the linear expansion magnitude and average thermal expansion coefficient, the measurements were carried out in the pressurizing direction at the time of powder compacting, and in a right-angled direction with respect to the pressurizing direction. The results are shown in Table 6.

TABLE 6

| | | Pressurizing Direction | | Right-angled Direction to Pressurizing Direction | |
|---|---|---|---|---|---|
| | Calcining Temp. (° C.) | Linear Expansion Magnitude (%) | Thermal Expansion Coefficient ($\times 10^{-6}$/° C.) | Linear Expansion Magnitude (%) | Thermal Expansion Coefficient ($\times 10^{-6}$/° C.) |
| Cordierite Sintered Body | 600 | 0.11 | 1.5 | 0.10 | 1.2 |
| | 750 | 0.14 | 1.9 | 0.12 | 1.5 |
| | 950 | 0.14 | 1.8 | 0.14 | 1.8 |
| | 1250 | 0.14 | 1.9 | 0.14 | 1.8 |
| Talc Powder Compact | | 1.48 | 19.0 | 0.51 | 6.6 |

In the linear expansion magnitudes and average thermal expansion coefficients of the cordierite calcined bodies, it is seen from Table 6 that no significant differences, which resulted from the pressurizing direction at the time of powder compacting, were recognized. And, it is apparent that the deformations would be less likely to occur in the cordierite calcined bodies at the time of service as a gas sealer, and that the degradation of the gas sealing properties that results from the migrations of the particles would be inhibited therein, because of the following: the linear expansion magnitudes were less than that of the talc powder compact in either one of the directions, in the pressurizing direction and in the right-angled direction to the pressurizing direction; and the average thermal expansion coefficients were small as well.

Testing Example No. 7

Using the alumina granules, aluminum titanate granules and cordierite granules that were used in each of the aforementioned testing examples, respectively, rod-shaped test specimens were made by powder compacting each of them in the same manner as Testing Example No. 2. The respective rod-shaped test specimens were impregnated with an inorganic-binder aqueous solution, in which sodium silicate was dissolved in a predetermined concentration, in a prescribed volume, and were then dried to turn them into powder compacts that included sodium silicate in an amount of 3% by mass.

After heating these powder compacts at 100° C. to remove the water content, they were heated at 450° C. for 1 hour to degrease the organic binder, and then they were further calcined at 600° C. for 1 hour to turn them into calcined bodies. Not only each of the calcined bodies was measured for the pore volume, median pore diameter and porosity in the same manner as Testing Example No. 1, but also the linear expansion magnitude and average thermal expansion coefficient were calculated in the same manner as Testing Example No. 2. The results are shown in Table 7. Note that the results of Testing Example Nos. 1-6 are given within the parentheses in Table 7.

TABLE 7

| | Pore Volume (mL/g) | Pore Diameter (μm) | Porosity (%) | Linear Expansion Magnitude (%) | Thermal Expansion Coefficient (×10$^{-6}$/° C.) |
|---|---|---|---|---|---|
| Alumina | 0.21 (0.27) | 0.06 (0.07) | 48 (52) | (0.56) | (7.3) |
| Aluminum Titanate | 0.19 (0.22) | 0.29 (0.34) | 41 (44) | 0.52 (0.55) | 6.7 (7.2) |
| Cordierite | 0.33 (0.37) | 0.28 (0.34) | 45 (51) | 0.16 (0.11) | 2.0 (1.5) |

It was ascertained that, even when the inorganic binder was used, anyone of the physical properties was satisfied fully as far as the addition amount fell in a range according to the present test. Moreover, the loads at the calcined bodies' compression breakage were upgraded as much as two-five times by means of adding the inorganic binder, compared with those in the case where the inorganic binder was not added.

INDUSTRIAL APPLICABILITY

The gas sensor according to the present invention can be used not only for oxygen sensors for detecting an oxygen concentration in automotive exhaust gases, but also for detecting a concentration of various gases.

The invention claimed is:

1. A gas sensor, comprising:
    a cylinder-shaped case defining an outermost surface of the gas sensor;
    a cylinder-shaped detector element inside of the case, comprising a solid electrolyte, and having opposite ends one of which is closed;
    a ring-shaped sealing portion filling a gap between and being in direct contact with an outer circumferential surface of the detector element and an inner circumferential surface of the case to seal the gap while maintaining a predetermined ventilation volume, thereby restricting the mixing of an interference gas with a gas to be measured; and
    the sealing portion comprising a calcined body of a powder compact of a spherically-shaped granulated powder chosen from alumina, aluminum titanate and cordierite.
2. The gas sensor as set forth in claim 1, wherein said sealing portion includes an inorganic binder.
3. A process for manufacturing a gas sensor, in which the gas sensor comprises
    a cylinder-shaped case defining an outermost surface of the gas sensor;
    a cylinder-shaped detector element inside of the case, comprising a solid electrolyte, and having opposite ends one of which is closed; and
    a ring-shaped sealing portion filling a gap between and being in direct contact with an outer circumferential surface of the detector element and an inner circumferential surface of the case to seal the gap while maintaining a predetermined ventilation volume, thereby restricting the mixing of an interference gas with a gas to be measured;
    the process comprising:
    subjecting a spherically-shaped granulated powder chosen from alumina, aluminum titanate and cordierite, to powder compacting, thereby forming a ring-shaped powder compact that includes an organic binder;
    loading the powder compact in a gap between and in direct contact with an outer circumferential surface of the detector element and an inner peripheral surface of the case, and then crimping the case from an outer circumferential surface thereof, thereby fixing the powder compact in the gap;
    removing the organic binder from the powder compact that has been fixed in the gap; and
    calcining the powder compact.
4. The process of manufacturing a gas sensor as set forth in claim 3, wherein an inorganic binder is further included in said powder compact.

* * * * *